US008829016B2

(12) United States Patent
Alanazi et al.

(10) Patent No.: US 8,829,016 B2
(45) Date of Patent: Sep. 9, 2014

(54) TRIAZOLE COMPOUNDS AS POTENTIAL ANTI-INFLAMMATORY AGENTS

(75) Inventors: Fars K. Alanazi, Riyadh (SA); Awwad A Radwan, Riyadh (SA); Ibrahim A. Alsarra, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/992,795

(22) PCT Filed: Apr. 20, 2012

(86) PCT No.: PCT/EP2012/001726
§ 371 (c)(1),
(2), (4) Date: Jun. 10, 2013

(87) PCT Pub. No.: WO2012/146362
PCT Pub. Date: Nov. 1, 2012

(65) Prior Publication Data
US 2014/0045902 A1    Feb. 13, 2014

(30) Foreign Application Priority Data

Apr. 26, 2011    (EP) .................... 11163672

(51) Int. Cl.
| | | |
|---|---|---|
| A01N 43/40 | (2006.01) | |
| A61K 31/435 | (2006.01) | |
| A01N 43/64 | (2006.01) | |
| A61K 31/41 | (2006.01) | |
| C07D 401/04 | (2006.01) | |
| C07D 401/14 | (2006.01) | |

(52) U.S. Cl.
CPC ............ *C07D 401/04* (2013.01); *C07D 401/14* (2013.01)
USPC ............................ 514/277; 514/383; 514/384

(58) Field of Classification Search
USPC .................................. 514/343, 277, 383, 384
See application file for complete search history.

(56) References Cited

U.S. PATENT DOCUMENTS 5,498,720 A * 3/1996 Lee ............................ 546/272.4

FOREIGN PATENT DOCUMENTS

| EP | 1273580 | 1/2003 |
| WO | 0010563 | 3/2000 |

OTHER PUBLICATIONS

Habib et al. ("Synthesis of Some Heterocyclic Derivatives of β-Sitosterol" Arch. Pharm. 323, 1990, 401-404).*
Bayrak H et al: "Synthesis of some new 1,2,4-triazoles, their Mannich and Schiff bases and evaluation of their antimicrobial activities", European Journal of Medicinal Chemistry, vol. 44, No. 3, Jun. 26, 2008, pp. 1057-1066.
Database Chemcats Chemical Abstracts Service, Jan. 12, 2011, XP002638696, Database accession No. 2023118602 Pyridine, 4-[5-(ethylthio)-4-phenyl-4H-1,2,4-triazol-3-yl]-CAS Registry No. (RN): 440638-06-2.
Database Caplus Chemical Abstracts Service, 2006, Kulish, S. M.; Knish, E. G.; Panasenko, 0. I.: "Alkylation and arylation of 5-(2-pyridinyl)-4-R-1,2,4-triazole-3-thion e derivatives", XP002638697, Medichna Khimiya, vol. 8, No. 2, 2006, pp. 112-114.
Penning et al: "Synthesis and Biological Evaluation of the 1,5-Diarylpyrazole Class of Cyclooxygenase-2 Inhibitors: Identification of 4-[5-(4-Methylphenyl)-3- (trifluoromethyl)-1H-pyrazol-1-yl]benzenes ul fonamide (SC-58635, Celecoxib", Journal of Medicinal Chemistry, vol. 40, Jan. 1, 1997, pp. 1347-1365.
PCT/EP2012/001726; PCT International Search Report and Written Opinion of the International Searching Authority mailed Jun. 13, 2012.

* cited by examiner

*Primary Examiner* — Yong Chong
(74) *Attorney, Agent, or Firm* — Renner, Otto, Boisselle & Sklar, LLP

(57) ABSTRACT

The present invention relates to a compound of formula 1 or 2

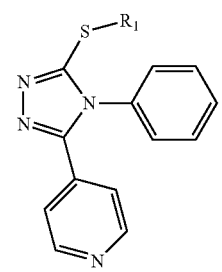

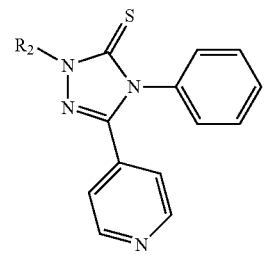

wherein $R_1$ represents straight-chain or branched $C_2$-$C_8$ alkyl, $C_2$-$C_8$ alkenyl, optionally substituted by at least one substituent selected from the group consisting of hydroxyl, amino or $C_1$-$C_6$ alkyl amino group, or $C_2$-$C_4$ alkynyl, optionally substituted by at least one substituent selected from the group consisting of hydroxyl, amino or $C_1$-$C_6$ alkyl amino group; and $R_2$ represents hydroxyl, $C_1$-$C_6$ alkyl, $C_1$-$C_6$ alkylcarbonyl, di($C_1$-$C_6$-alkyl)aminomethyl, $C_3$-$C_6$ heterocyclylmethyl or arylaminomethyl, wherein the aryl group is optionally substituted by at least one substituent selected from the group consisting of halogens and $C_1$-$C_6$ alkoxy as well as associated pharmaceutical compositions and uses of the compound or composition in therapy, in particular for the treatment of a disorder or a disease susceptible to inhibition of COX-2.

2 Claims, No Drawings

TRIAZOLE COMPOUNDS AS POTENTIAL ANTI-INFLAMMATORY AGENTS

The present application is a U.S. National Stage Application based on and claiming benefit under 35 U.S.C. §371 of PCT/EP2012/001726, filed 20 Apr. 2012, which in turn claims priority to European Application No. 11163672.6, filed 26 Apr. 2011, the entirety of both of which are hereby incorporated herein by reference.

The present invention relates to novel 4-phenyl-5-pyridine-4-yl-2,3-dihydro-3H-1,2,4-triazole-3-thione analogs which are selective inhibitors of cyclooxygenase-2 (COX-2 inhibitors) and thus potential anti-inflammatory agents.

Through the path of prostaglandin-thromboxane synthesis, the transformation of arachidonic acid to prostaglandin H2 (PGH2) is catalyzed by cytosolic prostaglandin G/H synthase, more commonly known as cyclooxygenase (COX). Prostaglandin H2 is an unstable intermediate and is further converted to one of many prostanoids, such as prostacyclin (PGI2) and thromboxane A2 (TXA2), by tissue-specific isomerases. The biosynthesis of these prostaglandins takes place in practically all tissues of the human body, eliciting a variety of pharmacological effects, some of them beneficial, as support of renal and platelet functions, gastrointestinal protection, and others non-beneficial as pain, fever and other symptoms associated with the inflammatory response. Since 1987, it has been established that the COX enzyme has 2 isoforms (Tanaka, Y. et al, *J. Biol. Chem.* 1987, 262, 1374), which are encoded by separate genes on different chromosomes.

Cyclooxygenase inhibition formed the basis for the success of non-steroidal anti-inflammatory drugs (NSAIDs) in treating a variety of pain syndromes. The drawback, however, was that, every year, 2% to 4% of patients taking NSAIDs suffer from symptomatic gastrointestinal ulcers and their complications (Silverstein, F. E. et al, *JAMA* 2000, 284, 1247). As the scientific research behind the COX enzyme progressed, it became apparent that COX-2 inhibition mediated the anti-inflammatory effects of NSAIDs, whereas COX-1 inhibition was responsible for the adverse effects on the gastrointestinal tract. It therefore became reasonable to assume that inhibiting COX-2 selectively would result in the same anti-inflammatory benefits that nonselective NSAIDs provided but with fewer gastrointestinal side effects. This enforced the interest of pharmaceutical industries in manufacturing new analgesic and anti-inflammatory medications known as selective COX-2 inhibitors or coxibs (Penning, T. D. et al, *J. Med. Chem.*, 1997, 40, 1347; Riendeau, D. et al, *J. Pharmacol. Exp. Ther.* 2002, 296, 558; Ranatunge, R. R. et al, *Bioorg. Med. Chem. Lett.* 2004, 14, 6049). A selective cyclooxygenase-2 (COX-2) inhibitor allows the desired synthesis of cytoprotective prostaglandins, in conjunction with a simultaneous inhibition of pro-inflammatory prostaglandin synthesis, thereby reducing dyspepsia and ulceration (Meade, E. A. et al, *J. Biol. Chem.* 1993, 268, 6610). However, emerging evidence suggests that adverse reactions such as gastrointestinal irritations or ulceration and renal liabilities are associated with prolonged use of COX-2 selective inhibitors. The adverse reactions have been attributed, at least in part, to COX-1 inhibition occurring with long-term exposure or at higher doses (Wolfe, M. M. et al, *Engl. J. Med.* 1999, 340, 1888).

COX-2 selective inhibitors are also known to suppress the synthesis of prostacyclin, a potent vasodilator, gastroprotectant, and platelet inhibitor, via inhibition of endothelial COX-2.

COX-2 selective inhibitors do not inhibit the production of thromboxane, a vasoconstrictor, and promoter of platelet aggregation, which is synthesized in platelets by COX-1 (Catella-Lawson and Crofford *Am. J. Med.* 2001, 110, 285; Mukherjee, D. et al, *JAMA* 2001, 286, 954). Therefore, COX-2 inhibitors intrinsically lack anti-thrombotic activity, and some cardiovascular liabilities have been associated preclinically with them (de Gaetano, G. et al, *Trends Pharm. Sci.* 2003, 24, 245).

Thus, there is still a need for novel, selective, and potent COX-2 inhibitors with an improved profile compared to current COX-2 inhibitors.

Diarylheterocycles, and other central ring pharmacophore templates, have been extensively studied as cyclooxygenase inhibitors. All these tricyclic molecules possess 1,2-diaryl substitution on a central four-, five-, or six-membered ring system such as cyclobutenone, pyrazole, 2-(5H)-furanone, isoxazole, pyridine, or thiazolidinedione (Friesen, R. W. et al, *J. Bioorg. Med. Chem. Lett.* 1996, 6, 2677; Prasit, P. et al, *J. Bioorg. Med. Chem. Lett.* 1999, 9, 1773; Talley, J. J. et al, *J. Med. Chem.* 2000, 43, 775). Ali, A. M. et al, *Arch Pharm Res* 2007, 30, 1186.).

Recently, a novel class of 6-alkylthio-substituted six-membered lactone (pyrane-2-one) rings has been designed and exhibited very good in vitro COX-2 inhibitory potency and selectivity (Praveen Rao, P. N. et al, *J. Med. Chem.* 2003, 46, 4872). Furthermore, differently substituted 1,2,4-triazole-3-thione derivatives exhibited anti-inflammatory activity (Tozkoparan, B. et al, *Arzneimittelforschung* 2005, 55, 533; Labanauskas, L. et al, *Farmaco* 2004, 59, 255; Labanauskas, L. et al, *Pharmazie* 2001, 56, 617). Structure based studies have been performed to indentify binding modes and important interactions of triaryl rings at the COX-2 active site (Plount-Price and Jorgensen, *J. Am. Chem. Soc.* 2000, 122, 9455; Soliva, R. et al, *J. Med. Chem.* 2003, 46, 1372; Pouplana, R. et al, J. Comput. Aided. Mol. Des. 2002, 16, 683). The triaryl ring moiety either containing a para-sulfonyl group (Friesen, R. W. et al, *J. Bioorg. Med. Chem. Lett.* 1996, 6, 2677; Prasit, P. et al, *Bioorg. Med. Chem. Lett.* 1999, 9, 1773; Talley, J. J. et al, *J. Med. Chem.* 2000, 43, 775; Ali, A. M. et al, *Arch Pharm Res* 2007, 30, 1186) or not containing a para-sulfonyl group (Portevin, B. et al, *J. Med. Chem.* 2000, 43, 4582; Sui, Z. *Bioorg. Med. Chem. Lett.* 2000, 10, 601; Dannhardt and Laufer, *Curr. Med. Chem.* 2000, 7, 1101; Barnett, J. W. et al, Eur. Patent, 1996, 0714895) has been recognized as a pharmacophore for selective COX-2 inhibition.

The object of the present invention is to provide for novel selective COX-2 inhibitors in order to make available further useful anti-inflammatory agents.

This object is solved by compounds as defined in claim 1. These novel compounds are 4-phenyl-5-pyridin-4-yl-2,3-dihydro-3H-1,2,4-triazole-3-thione analogs of the general formula (1) or (2)

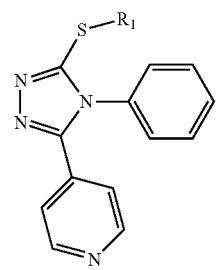

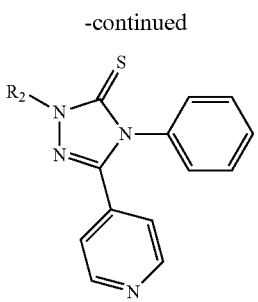

wherein

R$_1$ represents straight-chain or branched C$_2$-C$_8$ alkyl, C$_2$-C$_8$ alkenyl, optionally substituted by at least one substituent selected from the group consisting of hydroxyl, amino or C$_1$-C$_6$ alkyl amino group, or C$_2$-C$_4$ alkynyl, optionally substituted by at least one substituent selected from the group consisting of hydroxyl, amino or C$_1$-C$_6$ alkyl amino group; and R$_2$ represents hydroxyl, C$_1$-C$_6$ alkyl, C$_1$-C$_6$ alkylcarbonyl, di(C$_1$-C$_6$-alkyl)aminomethyl, C$_3$-C$_6$ heterocyclylmethyl or arylaminomethyl, wherein the aryl group is optionally substituted by at least one substituent selected from the group consisting of halogens and C$_1$-C$_6$ alkoxy.

Preferably, R$_1$ represents C$_5$-C$_6$ alkyl, C$_5$-C$_6$ alkenyl or C$_3$ alkynyl.

Most preferably, R$_1$ is selected from the group consisting of 1-pentyl, 2-pentyl, 3-pentyl, cyclopentyl, 1-hexyl, 2-hexyl, 3-hexyl, pent-4-enyl and propynyl.

R$_2$ is preferably selected either from the group consisting of hydroxymethyl, ethoxycarbonyl, dimethylaminomethyl, diethylaminomethyl, and pyrrolidinylmethyl, or from the group of unsubstituted and substituted phenylaminomethyl and benzylaminomethyl, wherein the phenyl or benzyl group may mono- or disubstituted by halogen.

In the context of the present invention, "halogen" means fluorine, chlorine or bromine, preferably chlorine.

The invention is also directed to a pharmaceutical composition comprising at least one of these novel compounds together with a pharmaceutically acceptable carrier or excipient.

The compound or the pharmaceutical composition of the invention is intended for use in therapy, in particular for the treatment of a disorder or disease susceptible to inhibition of COX-2, in particular to a disorder or disease associated with inflammation, or for the preparation of a medicament for these medical treatments. 4-phenyl-5-pyridine-4-yl-4H-1,2,4-triazole-3-thione can be obtained adopting published methods (Bayrak, H. et al, *Eur. J med. Chem.* 2009, 44, 1057). The compounds of the invention (1) and (2) are synthesized through the reaction of 4-phenyl-5-pyridine-4-yl-4H-1,2,4-triazole-3-thione with ethyl chloroformate in the presence of anhydrous sodium carbonate under reflux in a solvent such as DMF or dioxane. This reactive results in a compound of Formula (2) (R$_2$=ethylcarboxylate). The reaction of 4-phenyl-5-pyridine-4-yl-4H-1,2,4-triazole-3-thione with formaline solution results in the 2-hydroxymethyl derivative of formula (2) (R$_2$=hydroxymethyl). The reaction of 4-phenyl-5-pyridine-4-yl-4H-1,2,4-triazole-3-thione with several secondary aliphatic amines or primary aromatic amines in the presence of formaldehyde solution results in the corresponding Mannich base derivatives of formula (2) incorporating, for example, dimethylamine, diethylamine, pyrrolidine, N-methylethanolamine, p-bromoaniline, and p-chlorobenzylamine. Examples of the reaction solvents are dimethylformamide, ethanol, and dioxane. Preferably, the reaction proceeds at about room temperature. S-alkylation of 4-phenyl-5-pyridine-4-yl-4H-1,2,4-triazole-3-thione was performed by its reaction with several alkyl halides in basic media resulting in compounds of formula (1) incorporating for example methyl, 2-pentyl, pent-4-enyl, or 3-propynyl.

Scheme 1

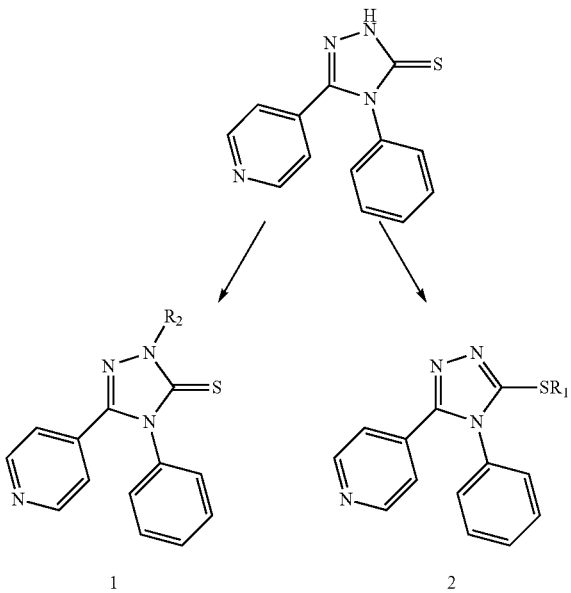

Anti-inflammatory activity was determined by the carrageenan-induced rat paw edema method described by Winter et al., *Proc. Soc. Exp. Biol. Med.* 1962, 111, 544, using male Sprague-Dawley rats weighing 150 to 200 g (6-8 weeks old). The protocol for the animal experiments performed was approved by the Research Ethics Committee and Animal Care and Use Committee, Govt. of Saudi Arabia. Compounds were administered intravenously in dimethyl sulfoxide solution. Paw edema was induced by intradermal injection of 50 μ. of 1% λ-carrageenan (Sigma, USA) into the subplantar region of the right hind paw, after one hour of compound administration. The paw volume was measured immediately after injection and after 2 hours using a plethysmometer (UGO-Basile, Italy). The control group received only the vehicle. Increase in paw volume was compared with that in the control group and percent inhibition was calculated taking the values in the control group as 0% inhibition.

An in vitro cyclooxygenase enzyme (COX) inhibition assay was done for the compounds of the invention to evaluated their ability to inhibit COX-1 and/or COX-2 enzymes (Sano, H. et al, *Bioorg. Med. Chem.* 2005, 13, 3079). Inhibition of the enzymes was determined with the colorimetric COX (ovine) inhibitor screening assay.

The biological evaluation of the new compounds of formula (1) or (2) of the invention revealed that the compounds are anti-inflammatory agents with potency as high as that of the celecoxib reference drug. The obtained results clearly point to the discovery of a new group of anti-inflammatory agents that induce their actions via selective inhibition of COX-2. The COX-2/COX-1 selectivity index of the potent individual compounds of the inventions was 2.5-5 which is higher than the selectivity index found with celecoxib being about 2.4. Also, besides its higher COX-2 inhibitor selectivity, most of the compounds of the present invention were more potent as COX-2 inhibitor than the celecoxib reference drug.

Molecular modeling and docking studies of the compounds of formula (1) and (2) in the active sites of both COX-1 (PDB code: 1CQE) (Picot, D. et al, *Nature* 1994, 367, 243) and COX-2 (PDB code: 1CX2) (Kurumbail, R.G. et al, *Nature* 1996, 384, 644-48) were performed in order to get further insight into the nature of interactions between the compounds and the active site amino acids to rationalize the obtained biological results. The compounds of formula (1) and (2) showed comparable interactions with equal or higher docking score at COX-2 compared to that of the co-crystallized SC-558 (selective COX-2 inhibitor). On the other hand, it showed variable interactions with lower docking score at COX-1 than that of the co-crystallized flurbiprofen (non-selective COX inhibitor). The results are in agreement with the high potency and high COX-2 selectivity, that obtained with its in vitro screening against COX-1 and COX-2, and also it is in qualitative agreement with their high activity measured in an anti-inflammatory model.

Therefore, those compounds of the formula (1) and (2) of the invention have the potential use as an anti-inflammatory medication.

The present invention also includes pharmaceutical compositions which, in addition to non-toxic, inert pharmaceutically suitable excipients, contain one or more active compounds according to the invention, or which consist of one or more active compounds according to the invention.

The present invention also includes pharmaceutical formulations in dosage units. This means that the formulations are in the form of individual parts, for example tablets, dragees, capsules, pills, and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

Non-toxic, inert pharmaceutically suitable excipients are to be understood as solid, semi-solid or liquid diluents, fillers and formulations auxiliaries of every kind. Tablets, dragees, capsules, pills, granules, solutions and sprays may be mentioned as preferred pharmaceutical formulations. Tablets, dragees, capsules and pills can contain the active compound or compounds alongside the customary excipients, such as (a) fillers and extenders, for example starches, lactose, sucrose, glucose, mannitol and silica, (b) binders, for example carboxy-methylcellulose, alginates, gelatin and polyvinylpyrrolidone, (c) humectants, for example agar-agar, calcium carbonate and sodium bicarbonate, (e) solution retarders, for example paraffin, and (f) resorption accelerators, for example quaternary ammonium compounds (g) wetting agents, for example cetyl alcohol and glycerol monostearate, (h) adsorbents for example kaolin and bentonite, and (i) lubricants, for example talc, calcium stearate and magnesium stearate and solid polyethylene glycols, or mixtures of the compounds listed under (a) to (i).

The tablets, dragees, capsules and pills can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the above mentioned excipients could also be in a micro-encapsulated form.

Solutions and emulsions for parenteral administration can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cotton seed oil, groundnut oil, maize germ oil, olive oil, castor oil and sesame oil, glycerol, glycerolformal, tetrahydrofurfuryl alcohol, polyethylene glycol and fatty acid esters of sorbitol, or mixtures of these substances, in a sterile form which is isotonic with blood.

The therapeutically active compounds should preferably be present in the above-mentioned pharmaceutical formulations in a concentration of about 0.1 to 99.5, preferably of about 0.5 to 95% by weight of the total mixture.

The above-mentioned pharmaceutical formulations can also contain other pharmaceutically active compounds in addition to the active compounds according to the invention. The above-mentioned pharmaceutical formulations are prepared in the customary manner according to known methods, for example by mixing the active compound or compounds with the excipient or excipients. The present invention also includes the use of the active compounds according to the invention, and of pharmaceutical formulations which contain one or more active compounds according to the invention in human and veterinary medicine. The actual dosage unit will be determined by such generally recognized factors as body weight of the patient and/or severity and type of pathological condition the patient might be suffering. With these considerations in mind, the dosage unit for a particular patient can be readily determined by the medical practitioner in accordance with the techniques known in the medical arts. The precise instructions for pharmaceutical administration of the compounds and agents according to the invention necessarily depend on the requirements of the individual case, the nature of treatment, and of course the opinion of the treating physician.

It will be understood by those skilled in the art that various modifications and substitutions may be made to the invention as described above without departing from the spirit and scope of the invention. Accordingly, it is understood that the present invention has been described by way of illustration and not limitation.

PREPARATION EXAMPLES

General Method for Preparation of Compounds 3-5

To a solution of 4-phenyl-5-pyridine-4-yl-4H-1,2,4-triazole-3-thione (2.54 g, 10 mmol) in absolute ethanol, 1 equiv. of sodium was added and the mixture was stirred at room temperature for 30 min. Then, the appropriate alkyl halide (20 mmol) was added and refluxed for 4 h.

After evaporating the solvent under reduced pressure a solid appeared. The solid was recrystallized from ethanol/water (1:1) to obtain the target compound.

Example 1

4-Phenyl-3-(prop-2-ynylthio)-5-pyridine-4-yl-2,4-dihydro-3H-1,2,4-triazole 3

Yield 2.26 g, 79%, mp 151-2° C.; IR (KBr) 3321, 2974, 1654, 1637, 826, 783, 698 cm$^{-1}$; $^1$H NMR, (DMSO-d6, δ ppm): 1.75 (1H, s, HC≡C), 4.1 (2H, s, ≡C-CH$_2$S), 7.25-7.30 (2H, m, C$_2$H and C$_6$H of phenyl), 7.30-7.35 (m, C$_3$H, C$_4$H and C$_5$H of phenyl), 7.6 (2H, d, C$_3$H and C$_5$H of pyridine), 8.57 (2H, d, C$_2$H and C$_6$H of pyridine). $^{13}$C NMR, (DMSO-d6, δ ppm): 22.12 (—CH$_2$—S), 72.78 (CH≡), 86.73 (≡C), 121.49 (2CH), 127.18 (CH), 130.36 (2CH), 130.59 (2CH), 133.58 (1CH), 133.99 (1CH), 150.25 (triazole C-3), 152.63 (2CH), 153.52 (triazole C-5). Anal. Calcd for C$_{16}$H$_{12}$N$_4$S: C, 65.73; H, 4.14; N, 19.16; S, 10.97. Found: C, 65.56; H, 3.92; N, 19.25; S, 11.09.

Example 2

3-[(Pent-2-yl)thio]-4-phenyl-5-pyridine-4-yl-2,4-dihydro-3H-1,2,4-triazole 4

Yield 2.61 g, 77%, mp 96-7° C.; IR (KBr) 3036, 2957, 1654, 1637, 836, 776, 694 cm$^{-1}$; $^1$H NMR, (CDCl$_3$, δ ppm): 0.85 (3H, t, CH$_3$), 1.3-1.4 (2H, m, CH$_2$), 1.4-1.7 (5H, m, CH$_3$ and CH$_2$), 3.5-4.1 (1H, m, CH), 7.0-7.15 (2H, m, C$_2$H and C$_6$H of phenyl), 7.15-7.30 (m, C$_3$H, C$_4$H and C$_5$H of phenyl), 7.5 (2H, d, C$_3$H and C$_5$H of pyridine), 8.4 (2H, d, C$_2$H and C$_6$H of pyridine). Anal. Calcd for C$_{18}$H$_{20}$N$_4$S: C, 66.63; H, 6.21; N, 17.27; S, 9.88. Found: C, 66.81; H, 6.35; N, 16.98; S, 10.03.

Example 3

3-[(Pent-4-enyl)thio]-4-phenyl-5-pyridine-4-yl-2,4-dihydro-3H-1,2,4-triazole 5

Yield 2.29 g, 73%, mp 132-3° C.; IR (KBr) 3037, 2932, 1654, 1640, 991, 914, 837, 776, 700 cm$^{-1}$; $^1$H NMR, (CDCl$_3$, δ ppm): 1.6-2.4 (4H, m, =CCH$_2$ CH$_2$), 4.7 (2H, d, =CH$_2$), 5.1 (1H, d, =CH), 7.0-7.15 (2H, m, C$_2$H and C$_6$H of phenyl), 7.15-7.30 (m, C$_3$H, C$_4$H and C$_5$H of phenyl), 7.5 (2H, d, C$_3$H and C$_5$H of pyridine), 8.4 (2H, d, C$_2$H and C$_6$H of pyridine). Anal. Calcd for C$_{18}$H$_{18}$N$_4$S: C, 67.05; H, 5.63; N, 17.38; S, 9.94. Found: C, 66.92; H, 5.75; N, 17.45; S, 10.06.

Example 4

Ethyl[4-phenyl-5-pyridine-4-yl-3-thioxo-2,4-dihydro-3H-1,2,4-triazole-2-yl]carboxylate 6

A mixture of 4-phenyl-5-pyridine-4-yl-4H-1,2,4-triazole-3-thione (2.54 g, 10 mmol), 0.9 g anhydrous sodium carbonate and ethyl chloroformate (10 mmol) in 5 ml DMF was refluxed for 7 h. The reaction mixture was cooled, then poured into ice-cold water. The solid formed was filtered off and recrystallized from acetic acid to give the title compound 7. Yield 2.7 g, 82%, mp 231-2° C.; IR (KBr) 3057, 1770, 1654, 1636, 1298, 828, 741, 697 cm$^{-1}$; $^1$H NMR (DMSO-d$_6$, δ, ppm): 1.6 (3H, t, CH$_3$), 4.3-4.8 (2H, q, CH$_2$—O), 7.0-7.1 (2H, m, C$_2$H and C$_6$H of phenyl), 7.1-7.25 (3H, m, C$_3$H, C$_4$H and C$_5$H of phenyl), 7.4 (2H, C$_3$H and C$_5$H of pyridine), 8.5 (2H, d, C$_2$H and C$_6$H of pyridine). Anal. Calcd for C$_{16}$H$_{14}$N$_4$O$_2$S: C, 58.88; H, 4.32; N, 17.17; S, 9.82. Found: C, 58.65; H, 4.53; N, 17.08; S, 9.61.

Example 5

2-Hydroxymethyl-4-phenyl-5-pyridine-4-yl-2,4-dihydro-3H-1,2,4-triazole-3-thione 7

A mixture of 4-phenyl-5-pyridine-4-yl-4H-1,2,4-triazole-3-thione (2.54 g, 10 mmol) and formaline (2 ml, 25 mmol.) in water (10 ml) was heated under reflux for 5 minutes cooled to room temperature and filtered. The solid was washed with cold water and dried to give the title compound 8. The crude was recrystallized from ethanol. Yield 2.2 g, 78%, mp 277-8° C.; IR (KBr) 3450, 3116, 2851, 1654, 1270, 830, 741, 695 cm$^{-1}$; $^1$H NMR (CDCl$_3$, δ, ppm): 3.3-3.8 (1H, broad s, OH), 5.7 (2H, s, NCH$_2$O), 7.05-7.25 (2H, m, C$_2$H and C$_6$H of phenyl), 7.25-7.4 (3H, m, C$_3$H, C$_4$H and C$_5$H of phenyl), 7.5 (2H, d, C$_3$H and C$_5$H of pyridine), 8.5 (2H, d, C$_2$H and C$_6$H of pyridine). Anal. Calcd for C$_{14}$H$_{12}$N$_4$OS: C, 59.14; H, 4.25; N, 19.70; S, 11.28. Found: C, 58.94; H, 4.75; N, 19.40; S, 11.35.

General Method for the Synthesis of Compounds 8 to 13

To a solution of 4-phenyl-5-pyridine-4-yl-4H-1,2,4-triazole-3-thione (2.54 g, 10 mmol) in dimethyl formamide, formaldehyde (37%, 1.55 mL) and an appropriate amine (10 mmol) were added and the mixture was stirred at room temperature for 2.5 h. Then, excess amount of pure water was added to this solution and the mixture was kept overnight in cold. The resulting solid separated was collected by filtration, washed with water, recrystallized from ethanol to yield the title compounds.

Example 6

2-Dimethylaminomethyl-4-phenyl-5-pyridine-4-yl-2,4-dihydro-3H-1,2,4-triazole-3-thione 8

Yield 2.52 g, 78%, mp 173-4° C.; IR (KBr) 3065, 2973, 1654, 1279, 832, 752, 697 cm$^{-1}$; $^1$H NMR, (CDCl$_3$, δ ppm): 2.7 (6H, s, (CH$_3$)$_2$N), 5.3 (2H, s, NCH$_2$N), 7.2-7.35 (2H, m, C$_2$H and C$_6$H of phenyl), 7.35-7.55 (3H, m, C$_3$H, C$_4$H and C$_5$H of phenyl), 7.6 (2H, d, C$_3$H and C$_5$H of pyridine), 8.6 (2H, d, C$_2$H and C$_6$H of pyridine). Anal. Calcd for C$_{16}$H$_{17}$N$_5$S: C, 61.71; H, 5.50; N, 22.49; S, 10.30. Found: C, 61.53; H, 5.74; N, 22.21; S, 10.62.

Example 7

2-Diethylaminomethyl-4-phenyl-5-pyridine-4-yl-2,4-dihydro-3H-1,2,4-triazole-3-thione 9

Yield 2.79 g, 83%, mp 216-17° C.; IR (KBr) 3076, 2965, 1654, 1279, 835, 748, 695 cm$^{-1}$; $^1$H NMR, (δ, ppm): 1.7 (6H, t, 2CH$_3$), 4.4-4.7 (4H, q, 2CH$_2$N), 5.7 (2H, s, NCH$_2$N), 7.0-7.2 (2H, m, C$_2$H and C$_6$H of phenyl), 7.2-7.4 (3H, m, C$_3$H, C$_4$H and C$_5$H of phenyl), 7.6 (2H, d, C$_3$H and C$_5$H of pyridine), 8.6 (2H, d, C$_2$H and C$_6$H of pyridine). Anal. Calcd for C$_{18}$H$_{21}$N$_5$S: C, 63.69; H, 6.24; N, 20.63; S, 9.45. Found: C, 63.45; H, 6.33; N, 20.42; S, 9.31.

Example 8

4-Phenyl-5-pyridine-4-yl-2-pyrrolidinylmethyl-2,4-dihydro-3H-1,2,4-triazole-3-thione 10

Yield 2.96 g, 90%, mp 139° C.; IR (KBr) 3116, 2836, 1654, 1636, 1270, 832, 742, 695 cm$^{-1}$; $^1$H NMR, (δ, ppm): 1.8 (4H, t, CH$_2$CH$_2$), 3.0 (4H, t, CH$_2$N CH$_2$), 5.7 (2H, s, NCH$_2$N), 7.0-7.2 (2H, m, C$_2$H and C$_6$H of phenyl), 7.2-7.4 (3H, m, C$_3$H, C$_4$H and C$_5$H of phenyl), 7.6 (2H, d, C$_3$H and C$_5$H of pyridine), 8.6 (2H, d, C$_2$H and C$_6$H of pyridine). Anal. Calcd for $C_{18}H_{19}N_5S$: C, 64.07; H, 5.68; N, 20.75; S, 9.50. Found: C, 64.21; H, 5.82; N, 20.58; S, 9.34.

Example 9

N-Methyl-N-[(4-phenyl-5-pyridine-4-yl-3-thioxo-2,4-dihydro-3H-1,2,4-triazol-2-y)methyl]-2-aminoethanol 11

Yield 2.52 g, 73%, mp 173-4° C.; IR (KBr) 3385, 3104, 2850, 1654, 1270, 868, 774, 694 cm$^{-1}$; $^1$H NMR, (CDCl$_3$, δ ppm): 1.8 (1H, broad s, OH), 2.8 (3H, s, NCH$_3$), 3.0 (2H, t, NCH$_2$), 4.0 (2H, t, CH$_2$O), 5.8 (2H, s, NCH$_2$N), 7.20-7.25 (2H, m, C$_2$H and C$_6$H of phenyl), 7.27-7.38 (3H, m, C$_3$H, C$_4$H and C$_5$H of phenyl), 7.6 (2H, d, C$_3$H and C$_5$H of pyridine), 8.6 (2H, d, C$_2$H and C$_6$H of pyridine). Anal. Calcd for $C_{17}H_{19}N_5OS$: C, 59.80; H, 5.61; N, 20.51; S, 9.39. Found: C, 59.71; H, 5.50; N, 20.32; S, 9.25.

Example 10

2-[(4-Bromophenylamino)methyl]-4-phenyl-5-pyridine-4-yl-2,4-dihydro-3H-1,2,4-triazole-3-thione 12

Yield 3.19 g, 75%, mp 208-9° C.; IR (KBr) 3032, 2944, 1654, 1636, 1276, 833, 807, 740 cm$^{-1}$; $^1$H NMR, (CDCl$_3$, δ ppm): 5.5 (1H, broad s, NH), 5.7 (2H, s, NCH$_2$N), 6.9-7.0 (2H, m, C$_2$H and C$_6$H of phenyl), 7.15-7.3 (m, C$_3$H, C$_4$H and C$_5$H of phenyl), 7.3 (2H, d, C$_2$H and C$_6$H of -p-bromophenyl), 7.4 (2H, d, C$_3$H and C$_5$H of -p-bromophenyl), 7.6 (2H, d, C$_3$H and C$_5$H of pyridine), 8.6 (2H, d, C$_2$H and C$_6$H of pyridine). $^{13}$C NMR, (CDCl$_3$, δppm): 65.44 (NCH$_2$N), 111.52 (C), 115.94 (2CH), 121.69 (2CH), 128.06 (CH), 130.12 (2CH), 130.46 (2CH), 132.19 (2CH), 132.86 (C), 134.10 (C), 143.73 (C), 146.86 (2CH), 150.10 (triazole C-3), 169.51 (triazole C-5). Anal. Calcd for $C_{20}H_{16}BrN_5S$: C, 54.80; H, 3.68; N, 15.98; S, 7.32. Found: C, 54.69; H, 3.51; N, 15.83; S, 7.12.

Example 11

2-[(4- Chlorobenzylamino)methyl]-4-phenyl-5-pyridine-4-yl-2,4-dihydro-3H-1,2,4-triazole-3-thione 13

Yield 2.89 g, 72%, mp 222-3° C.; IR (KBr) 3052, 2928, 1654, 1636, 1274, 828, 798, 697 cm$^{-1}$; $^1$H NMR, (CDCl$_3$, δ ppm): 1.9 (1H, broad s, NH), 4.5 (2H, s, benzylic CH$_2$), 5.8 (2H, s, NCH$_2$N), 7.12-7.17 (2H, m, C$_2$H and C$_6$H of phenyl), 7.21-7.26 (m, C$_3$H, C$_4$H and C$_5$H of phenyl), 7.29 (2H, d, C$_2$H and C$_6$H of -p-chlorophenyl), 7.38 (2H, d, C$_3$H and C$_5$H of -p-chlorophenyl), 7.55 (2H, d, C$_3$H and C$_5$H of pyridine), 8.59 (2H, d, C$_2$H and C$_6$H of pyridine). $^{13}$C NMR, (CDCl$_3$, δ ppm): 55.23 (benzylic CH$_2$N), 68.11 (NCH$_2$N), 121.56 (2CH), 128.06 (CH), 128.20 (2CH), 129.63 (2CH), 130.05 (2CH), 130.34 (2CH), 132.77 (C), 132.86 (C), 134.38 (C), 136.86 (C), 146.99 (2CH), 150.41 (triazole C-3), 170.09 (triazole C-5). Anal. Calcd for $C_{21}H_{18}ClN_5S$: C, 61.83; H, 4.45; N, 17.17; S, 7.86. Found: C, 61.71; H, 4.57; N, 17.01; S, 7.98.

Example 12

In Vivo Carrageenan Induced Rat Paw Edema Assay

Anti-inflammatory activity was determined by the carrageenan-induced rat paw edema method described by (Winter et al. *Proc. Soc. Exp. Biol. Med.* 1962, 111, 544). Male Sprague-Dawley rats weighing 150 to 200 g (6-8 weeks old) were used in groups of six animals per group for the experiments. The animals were housed in a room with temperature of 22±2° C. under a 12 h light/dark cycle. They were allowed free access to food and water ad libitum. The protocol for the animal experiments performed was approved by the Research Ethics Committee and Animal Care and Use Committee, Govt. of Saudi Arabia. Compounds were administered intravenously in dimethyl sulfoxide solution. Paw edema was induced by intradermal injection of 50 µl of 1% X-carrageenan (Sigma, USA) into the subplantar region of the right hind paw, after one hour of compound administration. The paw volume was measured immediately after injection and after 2 hours using a plethysmometer (UGO-Basile, Italy). The control group received only the vehicle. Increase in paw volume was compared with that in the control group and percent inhibition was calculated taking the values in the control group as 0% inhibition.

Example 13

In Vitro COX Inhibition Assay

The final compounds were evaluated for their ability to inhibit ovine COX-1 and COX-2 enzymes [50% percent inhibition is expressed in molar concentration (nmol)] (Sano, H. et al, Bioorg. Med. Chem. 2005, 13, 3079). Inhibition of the enzymes was determined with the colorimetric COX (ovine) inhibitor screening assay kit (Cayman Chemicals, USA) using ELISA reader.

TABLE 1

Percent inhibition of carrageenan paw edema (CPE) and COX-1 and COX-2 inhibitor activity of the compounds 3-13.

| | AI activity | | | | Selectivity |
|---|---|---|---|---|---|
| | % inhibition | % inhibition | IC$_{50}$ (nM) | | index (COX-1/ |
| Compound | at 1 hr | at 2 hr | COX-1 | COX-2 | COX-2) |
| 3 | 10 ± 5.4 | 12 ± 4.9 | 7.5 | 5.3 | 1.42 |
| 4 | 36 ± 2.1 | 50 ± 2.5 | 3.7 | 1.4 | 2.64 |
| 5 | 9 ± 1.3 | 38 ± 1.8 | 4.4 | 2.6 | 1.69 |
| 6 | 0.0 | 5 ± 1.8 | 9.2 | 7.8 | 1.18 |
| 7 | 25 ± 1.8 | 66 ± 2.6 | 3.5 | 0.8 | 4.38 |
| 8 | 51 ± 1.5 | 76 ± 2.8 | 3.1 | 0.9 | 3.44 |
| 9 | 45 ± 1.1 | 66 ± 1.2 | 3.8 | 1.1 | 3.46 |
| 10 | 62 ± 3.4 | 66 ± 1.5 | 3.7 | 0.9 | 4.11 |
| 11 | Zero | 16 ± 5.9 | 4.5 | 2.1 | 2.14 |
| 12 | 12.5 ± 1.6 | 29 ± 3.8 | 6.4 | 3.9 | 1.64 |
| 13 | 16 ± 5.7 | 19 ± 6.3 | 8.7 | 6.8 | 1.38 |
| Celecoxib | 50 ± 2.1 | 71.5 ± 3.7 | 4.1 | 1.9 | 2.16 |

Example 15

Docking

Molecular docking study was done using Surflex-Dock within Sybyl 8.1.1 on HPxw8400 workstation, linux_OS2x at laboratory of drug design, School of Pharmaceutical Sciences, Kitasato University, Tokyo, Japan. The crystal structures of the two isozymes COX-1 with fluorbiprofen (PDB entry code: 1cqe) (Picot, D. et al, *Nature* 1994, 367, 243) and the COX-2 with sc-558 (PDB entry code: 1cx2) (Kurumbail, R. G. et al, *Nature* 1996, 384, 644-48) were retrieved from the RCSB Protein Data Bank. Surflex-Dock uses an empirical scoring function and a patented search engine to dock ligands into a protein's binding site (Jain, A. N. *J. Med. Chem* 2003, 46, 499). A Protomol, which was used to guide molecular docking, is a computational representation of the intended binding site to which putative ligands are aligned. Protomols can be produced by one of three routes: (Ruppert, J. et al, *Protein Sci* 1997, 6, 524) (1) automatic: Surflex-Dock finds the largest cavity in the receptor protein; (2) ligand-based: a ligand in the same coordinate space as the receptor; (3) residue-based: specified residues in the receptor. Thus, a Protomol can be generated automatically or defined based on a cognate ligand or known active site. In the current paper, a Protomol was generated automatically. Two parameters determining the extent of the Protomol—a threshold parameter of 0.46 and a bloat parameter of 1 Å—were established. All the water molecules in 1cqe or 1cx2 (receptor) were deleted, and hydrogen atoms were added to themg (Muthas, D. et al, *J. Mol. Graph. Model.* 2008, 26, 1237; Clark, R. D. *J. Comput. Aided Mol. Des.* 2008, 22, 507). The protein structure was utilized in subsequent docking experiments without energy minimization. In addition, treatment of docking small molecules (ligands) was as follows: preparation of 3D structures of ligands using Ligprep software module (Schrodinger, Inc, New York, NY). During this preparation step, hydrogen atoms were explicitly added, all possible ionization states were generated between pH 6.0 and pH 8.0 using the apic module, and the 3D molecular structures were minimized with OPLS 2005 force-field in Schrodinger software suite.[49] Tautomers were also generated in this step. This preparation step was done on dell workstation under linux x86-32 at laboratory of drug design, School of pharmaceutical Sciences, Kitasato University, Tokyo, Japan. Charge calculation with energy minimization method: Powell; force field: tripos; charge: MMFF94; max iterations: 1,000; termination: 0.001 kcal/(mol*Å); root mean square (RMS) displacement: 0.001 Å; other parameters: treated by default. In the docking procedure, five additional starting conformations are used and ten binding poses per ligand were obtained, and the binding pose with the highest total score was taken into consideration for ligand-receptor interactions. Docking results were validated by finding the root mean squared deviation (RMSD) between the docking position calculated for sc-588 and flurobiprofen and that observed in their crystal structures.

TABLE 2

Calculated docking score for COX-1 and COX-2.

| Compound | Total docking score | |
| --- | --- | --- |
| | COX-1 | COX-2 |
| 3 | 6.13 | 6.31 |
| 4 | 7.56 | 8.36 |
| 5 | 7.23 | 9.15 |
| 6 | 5.42 | 7.87 |
| 7 | 4.59 | 6.63 |
| 8 | 5.56 | 8.60 |
| 9 | 6.21 | 9.37 |

TABLE 2-continued

Calculated docking score for COX-1 and COX-2.

| Compound | Total docking score | |
| --- | --- | --- |
| | COX-1 | COX-2 |
| 10 | 4.89 | 8.41 |
| 11 | 6.61 | 8.10 |
| 12 | 4.25 | 4.64 |
| 13 | 4.31 | 5.74 |
| Celecoxib | 4.31 | 7.99 |
| Flurbiprofen | 6.8 | 6.19 |

The invention claimed is:
1. A compound of formula 1 or 2

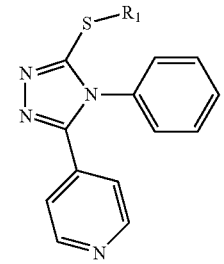

1

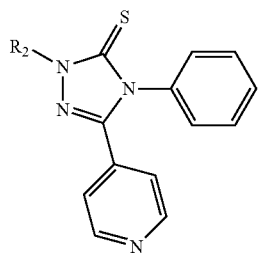

2 wherein
wherein $R_1$ is selected from the group consisting of 1-pentyl, 2-pentyl, 3-pentyl, cyclopentyl, 1-hexyl, 2-hexyl, 3-hexyl, pent-4-enyl and propynyl; and
$R_2$ is selected from the group consisting of hydroxymethyl, ethoxycarbonyl, dimethylaminomethyl, diethylaminomethyl, pyrrolidinylmethyl, unsubstituted and substituted phenylaminomethyl and benzylaminomethyl, wherein the phenyl or benzyl group is mono- or disubstituted by halogen.

2. A pharmaceutical composition comprising at least one compound of claim 1 together with a pharmaceutically acceptable carrier or excipient.

* * * * *